United States Patent
Komai et al.

(10) Patent No.: US 8,686,049 B2
(45) Date of Patent: Apr. 1, 2014

(54) AGENT FOR INCREASING TESTOSTERONE LEVEL

(75) Inventors: Michio Komai, Sendai (JP); Hitoshi Shirakawa, Sendai (JP); Yusuke Ohsaki, Hukuroi (JP); Tadashi Takumi, Sendai (JP); Asagi Ito, Sendai (JP); Toshiro Sato, Hukuroi (JP); Rumi Ozaki, Hukuroi (JP)

(73) Assignees: J. Oil Mills, Tokyo (JP); Tohoku University, Miyagi (JP)

( * ) Notice: Subject to any disclaimer, the term of this patent is extended or adjusted under 35 U.S.C. 154(b) by 851 days.

(21) Appl. No.: 12/305,403

(22) PCT Filed: May 21, 2007

(86) PCT No.: PCT/JP2007/060341
§ 371 (c)(1), (2), (4) Date: Dec. 18, 2008

(87) PCT Pub. No.: WO2007/148494
PCT Pub. Date: Dec. 27, 2007

(65) Prior Publication Data
US 2009/0209653 A1   Aug. 20, 2009

(30) Foreign Application Priority Data
Jun. 23, 2006 (JP) ................................. 2006-173455

(51) Int. Cl.
*A61K 31/122* (2006.01)

(52) U.S. Cl.
USPC .......................................................... 514/681

(58) Field of Classification Search
None
See application file for complete search history.

(56) References Cited

U.S. PATENT DOCUMENTS

2006/0058398 A1*  3/2006  Kamei et al.

FOREIGN PATENT DOCUMENTS

| JP | 10-165139 | 6/1998 |
|---|---|---|
| JP | 11-056232 | 3/1999 |
| JP | 11-127816 | 5/1999 |
| JP | 2003-063970 | 3/2003 |

OTHER PUBLICATIONS

Sirakawa et al., Biochemica et Biophysica Acta, 2006, vol. 1760, pp. 1482-1488, available online Jun. 6, 2006.*
Mayo Clinic Staff, "Male hypogonadism", MayoClinic.com Reprints, Dec. 9, 2010, pp. 1-10, downloaded from http://www.mayoclinic.com/health/male-hypogonadism/DS00300.*
Merriam-Webster online dictionary, "andropause", Merriam-Webster, downloaded from "http://www.merriam-webster.com/medical/andropause" on Nov. 19, 2011, p. 1 of 1.*
Rhoden et al., New England Journal of Medicine, 2004, vol. 350, pp. 482-492.*
Vitamin K deficiency reduces testosterone production in the testis through down-regulation of the Cyp11a a cholesterol side chain cleavage enzyme in rats; Hitoshi Shirakawa; Yusuke Ohsaki; Yoshihiko Minegishi; Naofumi Takumi: Kousaku Ohinata; Yuji Furukawa; Takeo Mizutani; Michio Komai; Biochimica et Biophysica Acta 1760 (2006) pp. 1482-1488.
Recent Topics in the Studies of Laboratory of Nutrition, Tohoku University: Newly Clarified Function of Vitamin K; Michio Komai; Yusuke Ohaski; Yoshihiko Minegishi; Naofumi Takumi; Yuji Furukawa and Hitoshi Shirakawa; Tohoku Journal of Agricultural Research; Vo. 57. No. 1, Nov. 2006; pp. 19-31.

* cited by examiner

*Primary Examiner* — Savitha Rao
*Assistant Examiner* — Gregg Polansky
(74) *Attorney, Agent, or Firm* — Kohn & Associates, PLLC

(57) ABSTRACT

Provided is a substance which is a safer and more commonly-consumed food ingredient that increase the testosterone level. The testosterone enhancer of the invention comprises vitamin K as an active ingredient. The vitamin is preferably menaquinone-4 and/or menaquinone-7. This enhancer is useful as pharmaceutical agents, supplements, health foods or functional foods for the prevention, amelioration and/or treatment of a condition or disease induced by the decreased testosterone level.

2 Claims, 5 Drawing Sheets mean±SE
n = 8 mean±SE
n = 7-8
**; p<0.01

AGENT FOR INCREASING TESTOSTERONE LEVEL

CROSS-REFERENCE TO RELATED APPLICATIONS

This application claims the benefit of priority to PCT/JP07/60341, filed May 21, 2007, which claims the benefit of priority under 35 U.S.C. Section 119(e) of Japan Serial No. 2006-173455, filed Jun. 23, 2006, which is incorporated herein by reference.

BACKGROUND OF THE INVENTION (1) Field of the Invention

The present invention relates to a testosterone enhancer. In particular, the present invention relates to a composition that increases endogenous testosterone.

(2) Description of Related Art

Testosterone, which is a type of androgenic hormone, widely contributes to muscle growth, cognitive functions, blood vessel flexibility, lipid metabolism, reproductive functions, and the like. Although testosterone secretion decreases with age, presence of endocrine disruptors also affects secretion. A recent DNA microarray analysis of germ-free rats in an extreme vitamin K deficient state suggests a possibility of menaquinone-4 contributing to testosterone biosynthesis ($8^{th}$ Vitamin K and Bone Meeting Records, pages 87 to 89, Dec. 10, 2005, Eisai Co., Ltd.; and Shirakawa, et al., Biochim. Biophys. Acta Vitamin K deficiency reduces testosterone production in the testis through down-regulation of the Cyp11a a cholesterol side chain cleavage enzyme in rats, ARTICLE In Press, Accepted Manuscript, Available online 6, Jun. 2006).

Indications show that, when testosterone secretion decreases, concentration and motivation decrease. Memory becomes poor, and strength, micturition, and male sexual functions also deteriorate. In recent years, patients suffering from male climacteric disorder have increased. In male climacteric disorder, blood testosterone level decreases as a result of hypogonadism, causing symptoms such as those described above.

One treatment for male climacteric disorder is hormone replacement therapy in which a patient is injected with testosterone formulas. However, the injection causes a rapid increase in the blood testosterone level and may actually cause illness. The rapid increase in hormone levels may cause adverse side effects affecting the prostrate, blood vessels, liver, lungs, and the like. Therefore, the hormone replacement therapy sometimes uses a transdermal skin patch through which testosterone is slowly released.

In addition to testosterone being replaced from outside as described above, following methods are proposed to boost the testosterone level in the body: intake of benzyl glucosinolates and benzyl isothiocyanates found in maca and the like (Japanese Patent Application Laid-open No. 2005-306754); intake of a mixture of maca and antlers (Japanese Patent Application Laid-open No. 2003-523945); and intake of substituted pyrazole compounds (Japanese Patent Application Laid-open No. 2005-504093).

BRIEF DESCRIPTION OF THE INVENTION

The above-described compositions achieving a testosterone enhancing effect are natural medicines or chemically synthesized drugs. Although commonly-consumed, safe food ingredients or nutrients that increase the blood testosterone level are preferable, such substances are not currently known. Therefore, a substance is desired that is a safer and more commonly-consumed food ingredient increasing the testosterone level.

It is shown herein that vitamin K1 or vitamin K2 ingested through foods is converted to menaquinone-4 in tissues. Because testes have a particularly high concentration of menaquinone-4, the function of vitamin K in the testes is herein determined. Through such research, it has been discovered that the blood testosterone level can be increased through intake of vitamin K, thereby arriving at the invention. In other words, the invention provides a testosterone enhancer including vitamin K.

Conventionally-known functions provided by vitamin K include maintaining normal blood coagulation, enhancing bone formation, controlling bone resorption, preventing arteriosclerosis by preventing coalification of arteries, and treating liver disease. Vitamin K is not known at all to cause increase in estrogen levels. Although Non-patent Documents 1 and 2 suggest that vitamin K contributes to the biosynthesis of testosterone, increase in testosterone through administration of vitamin K was not foreseen.

The above-described vitamin K is preferably vitamin K2.

The above-described vitamin K is more preferably menaquinone-4 and/or menaquinone-7.

The invention provides medicines made from the above-described testosterone enhancer that prevents, improves, and/or treats symptoms and diseases caused by decreased testosterone.

The invention also provides supplements, health foods, and functional foods to which the testosterone enhancer has been added.

In the invention, the blood testosterone level can be easily increased through intake of vitamin K that is highly safe for humans. Because lipid-soluble vitamin K is more easily accumulated in the body than conventional testosterone formulas, effects are long-lasting. As a result of the testosterone level returning to an ordinary level, functions to which vitamin K contributes (muscle strength, sexual functions, and the like) can be maintained or improved. Alternatively, symptoms and diseases, such as male climacteric disorder occurring because of decreased testosterone, can be improved. The testosterone enhancer of the invention can easily be consumed regularly as functional foods or health foods. Therefore, prevention of the above-described symptoms and diseases can also be attempted.

Although vitamin K intake required by a person per day is 55 µg to 80 µg (Dietary Reference Intakes for Japanese, 2005), a tolerable upper intake level is a very high level of 30 mg. Vitamin K is a very safe substance. Therefore, the testosterone enhancer of the invention is superior in safety than conventionally known testosterone enhancers.

BRIEF DESCRIPTION OF THE SEVERAL VIEWS OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
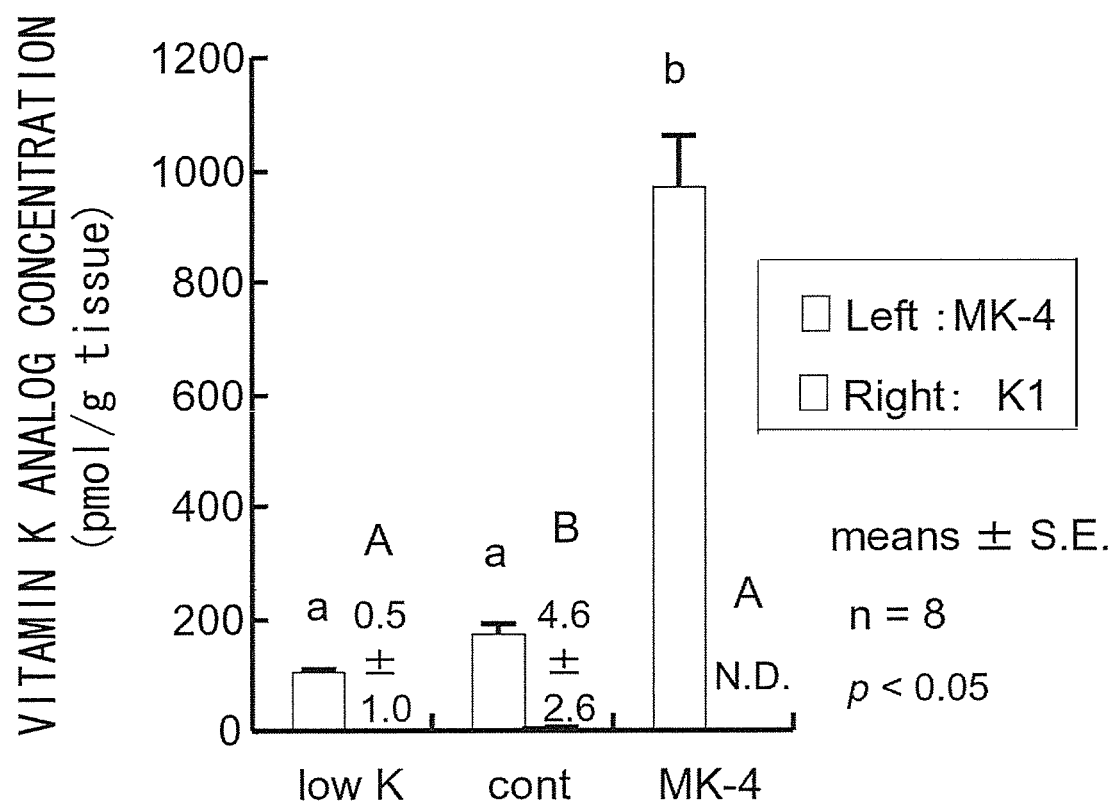
FIG. 1 is a diagram of a comparison of vitamin K analog concentrations in rat testes when rats are administered an MK-4 diet in adherence to Example 1, and a control diet and a low vitamin K diet as comparison examples.

A testosterone enhancer according to an embodiment of the invention will hereafter be described in detail. Vitamin K used in the testosterone enhancer of the invention is vitamin K1, vitamin K2, and vitamin K3. Vitamin K1 (also referred to as phylloquinone) is found at high levels in green and yellow vegetables, legumes, vegetable oils, seaweeds, seafood, and the like. Vitamin K2 (also referred to as menaquinone) is produced by microorganisms and is found at high levels in natto (Japanese fermented soybeans) and dairy products, such as cheese. Bacteria in the intestinal tract also produce vitamin K2. In vitamin K2, homologues from menaquinone-4 (MK-4) to menaquinone-15 (MK-15) are present depending on a length of isoprenoid side chains on naphthoquinone moiety. For example, high levels of MK-6 to MK-9 are found in cheese, and high levels of MK-7 in natto. Vitamin K3 (also referred to as menadione) is synthetic.

Side effects become a concern when vitamin K3 is ingested at high levels. Therefore, in terms of dietary experience, vitamin K1 extracted and purified from vegetables, and vitamin K2 extracted from fermenting substances using natto bacillus and the like are safer and, therefore, preferable. Vitamin K2, which can be cheaply and easily manufactured, is more preferable. Menaquinone-4 approved as a food additive and/or menaquinone-7 used as a food ingredient are particularly preferable. Vitamin K1 and vitamin K2 ingested through foods are known to be converted to menaquinone-4 in the body.

Manufacturing methods of each vitamin K are not particularly limited. Commercially available items can also be used without restrictions. Specifically, fermentation using microorganisms, extraction and purification from food products, and chemical synthesis can be used.

Vitamin K1 is extracted and purified using known methods (such as Japanese Patent Application Laid-open No. Heisei 5-155803) from green perilla, perilla, mulukhiya, parsely, edible chrysanthemum leaves, komatsuna (Japanese mustard spinach), spinach, mitsuba (Japanese wild parsely), alfalfa, hazelnut leaves, chestnut leaves, barley spears, oat spears, cabbage, broccoli, cauliflower, tomatoes, plant oils (soybean oil, rapeseed oil, sesame oil, peanut oil, corn oil, safflower oil, sunflower oil, rice bran oil, and olive oil) and the like. Vitamin K1 can also be obtained through synthesis. Vitamin K1 is a light yellow, lipid-soluble oil that is thermally stable, but unstable to light. Vitamin K may be in an oxide form.

Vitamin K2 is produced by fermentation using microorganisms, such as natto bacillus, using methods described in Japanese Patent Application Laid-open Nos. Heisei 08-073396, Heisei 11-92414, Heisei 10-295393, 2001-136959, and the like.

Vitamin K content included in the testosterone enhancer of the invention changes depending on the amount of composition ingested. The content is ordinarily in a range of 0.0001% to 100% by weight, preferably 0.001% to 90% by weight, more preferably 0.01% to 70% by weight, and even more preferably 1% to 50% by weight. When the content is less than 0.0001%, an amount required to achieve the testosterone enhancement effect may not be ingested.

In addition to the essential ingredient that is vitamin K, the testosterone enhancer of the invention can include one or more types of substances known to increase testosterone. The substances are, for example, plants such as maca, natural medicines such as deer antlers, extracts from such plants and natural medicines, benzyl glucosinolates, benzyl isothiocyanates, and substituted pyrazole compounds.

In addition to the essential ingredient that is vitamin K, and appropriate testosterone-enhancing substances, the testosterone enhancer of the invention can include carriers, excipients, auxiliary agents, and the like that can be used pharmacologically, within a range that does not inhibit the effects of the invention.

Specifically, the following can be included: carriers and excipients, such as lactose, sucrose, fructose, glucose, glucose hydrate, white sugar, purified sucrose, erythritol, xylitol, sorbitol, mannitol, palatinose, palatinit, powdered reduced malt sugar, starch syrup, carmellose, dextrin, corn starch, pregelatinized starch, partially pregelatinized starch, potato starch, hydroxypropyl starch, amino acids, kaolins, silicic acid anhydride, silicic acids, aluminum silicates, sodium bicarbonate, calcium phosphate, calcium dihydrogen phosphate, calcium carbonate, magnesium oxides, aluminum hydroxide, fatty acids, fatty acid salts, fatty acid monoglyceride and diglyceride, alcohols, vegetable oil, olive oil, soybean oil, corn oil, fatty oil, oils and fats, viscous paraffin, propylene glycol, ethylene glycol, polyethylene glycol, and glycerin; binders, such as crystalline cellulose, crystalline cellulose carmellose sodium, methyl cellulose, hydroxypropyl cellulose, low-substituted hydroxypropyl cellulose, hydroxypropyl methyl cellulose, hydroxypropyl methylcellulose phthalate, hydroxypropyl methylcellulose acetate succinate, carmellose sodium, ethyl cellulose, carboxymethyl ethyl cellulose, hydroxyethyl cellulose, wheat starch, rice starch, corn starch, potato starch, pregelatinized starch, partially pregelatinized starch, hydroxypropyl starch, dextrin, pullulan, polyvinylpyrrolidone, alkyl amino methacrylate copolymer E, alkyl amino methacrylate copolymer RS, methacrylic acid copolymer L, methacrylic acid copolymer, polyvinylacetal diethylamino acetate, polyvinyl alcohol, acacia gum, powdered acacia, agar, gelatin, white shellac, tragacanth, and macrogol; lubricants, such as wheat starch, rice starch, corn starch, synthetic aluminosilicate, dried aluminum hydroxide gel, magnesium metasilicate aluminate, calcium hydrogen phosphate, anhydrous calcium hydrogen phosphate, waxes, hydrogenated vegetable oil, polyethylene glycol, light anhydrous silicic acid, synthetic aluminosilicate, stearic acid, macrogol, talc, magnesium stearate, calcium stearate, aqueous silicon dioxide, and sucrose fatty acid ester; disintegrants, such as crystalline cellulose, methyl cellulose, low-substituted hydroxypropyl cellulose, carmellose, carmellose calcium, carmellose sodium, croscarmellose sodium, wheat starch, rice starch, corn starch, potato starch, partially pregelatinized starch, hydroxypropyl starch, sodium carboxymethyl starch, and tragacanth; surfactants, such as soybean lectin, sucrose fatty acid ester, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, and lauromacrogol; emulsifiers; solubilizers, such as sodium phosphate; absorption promoter; pH adjusters, such as hydrochloric acid, citric acid, sodium citrate, acetic acid, tartaric acid, sodium hydroxide, potassium hydroxide, sodium hydrogen carbonate, sodium carbonate, and lactic acid; brighteners, such as natural resin; stabilizers; antioxidants; preservatives; wetting agents; colorants; flavoring agents; soothing agents; and the like.

The testosterone enhancer of the invention is used for medicines, supplements, functional foods, and health foods. Therefore, the testosterone enhancer is processed into liquid, powder, granules, tablets, capsules, syrups, and the like. Because vitamin K is lipid-soluble, the testosterone enhancer is preferably in tablet or capsule form.

The testosterone enhancer of the invention can be directly added to basic ingredients of common processed foods, such as bread, rice, soup, prepared foods, snacks, and candy, during manufacturing.

A method of administering the testosterone enhancer of the invention for the usage of medicines is not particularly limited. For example, oral ingestion, dermal administration, liquid transport, and injection (intramuscular, intraperitoneal, hypodermic, and intravenous) can be used. Preferably, the testosterone enhancer is orally ingested in tablet or capsule form because less stress is placed on the patient.

Dosage and administration of the testosterone enhancer of the invention for the usage of medicines can be determined through consideration of symptoms experienced by the patient, weight of the patient, administration interval, administration method, and various factors affecting other clinical effects. Typically, the daily vitamin K intake for an adult male is 10 μg to 100 mg, and preferably 20 μg to 100 mg. When vitamin K is used for treatment, 6 mg to 100 mg can be used.

When the testosterone enhancer of the invention is used for supplements, functional foods, health foods, and ordinary foods, in view of safety, the daily vitamin K intake for an adult male is preferably 10 μg to 30 mg, and more preferably 50 μg to 6 mg.

In addition to humans, the testosterone enhancer of the invention can be used for medicines and functional foods ingested by animals, such as male domestic livestock and pets. The administration method can be non-oral administration, such as injection, and oral administration, such as through functional foods and formulated feed.

When a male mammal including humans ingests the testosterone enhancer of the invention, medicines produced using the testosterone enhancer, and foods including the testosterone enhancer, vitamin K increases testosterone. Therefore, the testosterone enhancer of the present invention is expected to achieve effects as treatment or preventative medicine for primary and secondary hypogonadism, and testosterone deficiency caused by aging or environmental factors. The testosterone enhancer of the invention can prevent, improve, and/or treat various diseases caused by decreased testosterone. In particular, prevention, improvement, and/or treatment of deterioration in muscles, cognitive functions, concentration, motivation, blood vessel flexibility, lipid metabolism, reproductive functions, male sexual functions, micturition, and the like can be expected.

The invention is further described in detail by reference to the following experimental examples. These examples are provided for the purpose of illustration only, and are not intended to be limiting unless otherwise specified. Thus, the present invention should in no way be construed as being limited to the following examples, but rather, be construed to encompass any and all variations which become evident as a result of the teaching provided herein.

Example 1

Blood testosterone enhancement effect of the testosterone enhancer of the present invention was studied using ordinary rats. An ordinary rat is a rat in which extreme vitamin K deficiency does not occur even when feed does not include vitamin K because the rat absorbs vitamin K produced by bacteria in its intestinal tract. The ordinary rat is a model extrapolating to a human living an ordinary life.

Materials and Methods
I Preparation of Model Animals
Breeding Experimental Animals Experimental animals and breeding conditions are as follows:
Experimental animals: ordinary rats (Wistar/Std, eight-week-old males)
Breeding environment: bred in a breeding room set to a temperature of 23° C., humidity of 50±5%, and a 12-hour light/dark cycle in which lights were turned on at 8 AM and turned off at 8 PM.

As experimental dietary groups, the following three groups were provided.
(1) Low K dietary group (no vitamin K was added)
(2) Control dietary group (vitamin K1 of 0.75 mg/kg was added)
(3) MK-4 added dietary group (menaquinone-4 of 75 mg/kg was added)

Here, the amount of vitamin K1 in the control diet was a vitamin K1 concentration used in a standard purified AIN93G diet. Therefore, the control dietary group refers to a standard diet including the amount of vitamin K ingested through ordinary rat feed. The menaquinone-4 added to the MK-4 added dietary group was Menatetrenone (Nisshin Pharma Inc.).

In each experimental diet, vitamin K1 or menaquinone-4 (also referred to, hereinafter, as MK-4) was added to achieve composition proportions shown in Table 1 and evenly mixed. The compositions of the experimental diets used are shown in Table 1.

TABLE 1

| | Composition (%) |
|---|---|
| Experimental Diet Composition | |
| Cornstarch | 52.9486 |
| Casein | 20 |
| Sucrose | 10 |
| Soybean oil | 7 |
| Cellulose | 5 |
| Mineral mixture | 3.5 |
| Vitamin mixture (original preparation) | 1 |
| L-cystine | 0.3 |
| Choline bitartrate | 0.25 |
| Tertiary butylhydroquinone | 0.0014 |
| Vitamin Mixture Composition | |
| Vitamin A | 40000 IU |
| Vitamin $B_{12}$ | 0.25 mg |
| Vitamin $D_3$ | 10000 IU |
| Vitamin E | 750 IU |
| Thiamin hydrochloride | 60 mg |
| Riboflavin | 60 mg |
| Pyridoxal hydrochloride | 70 mg |
| Nicotinic acid | 300 mg |
| D-panthotenic acid Ca | 160 mg |
| Folic acid | 20 mg |

TABLE 1-continued

| | Composition (%) |
|---|---|
| D-biotin | 2 mg |
| Vitamin K | * |

* Vitamin K was not added to the low K diet group. 7.5 mg of vitamin K1 was added to the control diet group. 750 mg of MK-4 was added to the MK-4 added diet group. The overall amount was adjusted to 100 g using sucrose, forming a vitamin mixture.

In the breeding method, preparatory breeding was performed in which the rats have free access to feed and water for three to five days. A commercially-available solid feed (product name: MR Labostock by Nosan Corp.) was used. Each experimental diet group includes four rats that were colony-bred in a wire mesh cage. After the preparatory breeding, the rats were fed respective experimental diets and bred for 35 days with free access to feed and water. Blood samples were taken, and testes were removed.

II Vitamin K Content Measurement
Preparing HPLC Measurement Sample

One gram of tissue was precisely measured and placed in a stoppered brown centrifuge tube. Two milliliters of 66% IPA solution was added. The sample was then homogenized in a Polytron homogenizer (Biotron) on ice. During homogenization, homogenates attached to the shaft were rinsed off with 3 ml of 66% IPA solution and added to the sample. With 5 ml of hexane, 1 ml of a hexane solution including 9.96 ng/ml or 996 ng/ml of MK-3 as the internal standard was added. The mixture was shaken for five minutes and extracted.

Subsequently, the mixture was centrifuged (3000 rpm at 4° C. for 5 minutes), and 5 ml of an upper hexane layer was separately placed in a brown test tube. The separated hexane layer was evaporated under reduced pressure by a centrifugal concentrator. The dried, solid hexane layer was again dissolved into 2 ml of hexane. The sample was applied to a Sep-pak silica cartridge (Waters Corp.) that had been cleaned in advance by 10 ml of a hexane-ether (96:4, v/v) solution and 10 ml of hexane.

After the cartridge was cleaned by the 10 ml of hexane, K groups were eluted by 5 ml of the hexane-ether (96:4, v/v) solution. After the mixture was again dried by the centrifugal concentrator, 200 µl (2 ml when an internal standard of 996 ng/ml of MK-3 was used) of ethanol was added to the residue, and the residue was dissolved. Particles were removed by a 0.5 µm filter (DISMIC03JP050AN, ADVANTEC). The filtered mixture was served as the HPLC measurement sample.

HPLC Measurement Conditions

The vitamin K homologues in the prepared HPLC sample are non-fluorescent, oxidized types. The vitamin K groups become fluorescent, reduced types as a result of the sample being separated by HPLC and platinum catalyst column being used. Quantities of the vitamin K groups were determined by an HPLC-reduction fluorescence method that measures fluorescence intensity of the sample. The vitamin K groups were determined as a relative value of MK-3 that was the internal standard.

Vitamin K Measurement System by HPLC

The vitamin K measurement system for measurement by HPLC is as follows:
HPLC apparatus: Waters 600E System (Waters Corp.)
Column: Puresil C18, 5 µm, 120 A, 4.6 mm×50 mm (Waters Corp.)
Column heater: Column Heater (Bio-Rad Laboratories)
Column heater temperature: 50° C.
Reduction device: Platinum Reduction Column IRICA-RC-10-1 (IRICA Corp.)
Fluorescence detector: F-1000 (Hitachi, Ltd., detection wavelengths Ex 240 nm, Em 430 nm)
Recorder: D-2000 (Hitachi, Ltd.)
Analysis conditions: Mobile phase MeOH-EtOH (8:2), flow rate 1.0 ml/min In the method, the HPLC-reduction fluorescence method is used in which the non-fluorescent, oxidized type vitamin K groups become fluorescent, reduced types through use of the platinum catalyst column. The fluorescence intensity of the vitamin K groups was measured. Therefore, a state in which oxygen was dissolved in the mobile phase adversely affects reduction. The dissolved oxygen was removed by ultrasonic waves being applied to the mobile phase under reduced pressure in advance. Nitrogen gas (200 ml/min or more) was bubbled from 2 hours before measurement until measurement was completed.

III RNA Measurement
Total RNA Preparation

Approximately 0.1 g of testis of each individual rat was placed in a dedicated tube. One milliliter of ISOGEN (NIP-PONGENE Co., Ltd.) as an RNA extracting reagent was added to the testes. The mixture was homogenized in the Polytron homogenizer. The homogenates were transferred to an eppendorf tube and left at room temperature for five minutes. Then, 200 µl of chloroform was added to the homogenates, and the mixture was vigorously stirred by a vortex for 15 seconds. After the mixture had been left at rest for two to three minutes, the mixture was centrifuged (13000 rpm at 4° C. for 15 minutes), thereby separating into three layers. Only the uppermost layer was taken. Five hundred microliters of IPA was added to the uppermost layer. The mixture was lightly shaken in a vertical direction and left for 10 minutes.

The mixture was centrifuged (13000 rpm at 4° C. for 15 minutes) again. Deposits formed as a result of centrifugal separation were rinsed twice with 1000 µl and 500 µl of 75% ethanol. The deposits were dissolved in 300 µl of DEPC-dH$_2$O. A portion of the dissolved deposits was used for absorbance measurement (260 nm and 280 nm) and agarose gel electrophoresis (0.7% TAE agarose gel at 150V for 35 minutes). RNA concentration and purity were tested.

cDNA Preparation by Reverse Transcription Reaction

The RNA obtained from each individual rat was dissolved by DEPC-dH$_2$O to be 1 µg/µl. The RNA solution was divided into two PCR tubes such that each PCR tube contained 4 µl of the RNA solution. One tube was prepared for RT(-) in which reverse trascriptase was not added, the other for checking whether genome DNA was included.

A mixture in which 1 µl of Oligo(dT)$_{20}$ (50 µM) and 1 µl of 10 mM dNTPmix (dATP, dGTP, dCTP, and dTTP) were added to 10 µl of DEPC-dH$_2$O was infused into each tube. The tubes were set in a PCR thermal cycler (TaKaRa Bio Inc.) and heated at 65° C. for 5 minutes.

After being heated and then placed on ice for one minute or more, the tubes were spun down. A mixture including 4 µl of 5× First-Strand Buffer, 1 µl of 0.1M DTT, 0.5 µl of RNase OUT, and 0.5 µl of Super Script III (dH$_2$O was used for RT(-)) was added to each tube. The tubes were again set in the thermal cycler, and reverse transcription reaction was performed at 50° C. for 60 minutes and at 70° C. for 15 minutes. cDNA samples were thereby obtained.

Determinate Quantity RT-PCR

The cDNA solution prepared by reverse transcription reaction that has been diluted 100 times was used as a sample. SYBR Premix Ex Taq (Perfect Real Time) (TaKaRa Bio Inc.) was used as the reactant. Twenty-five microliters of SYBR Premix Ex Taq, 1 µl of Rox Reference Dye, 1.5 µl each of forward and reverse primer solutions, and 17 µl of dH$_2$O were added to 4 µl of the sample or standard cDNA. Twenty-four microliters of the above-described reaction solution were infused into each of the two wells of a MicroAmp Optical 96-well Reaction Plate, and the MicroAmp Optical 96-well Reaction Plate was set in an ABI PRISM 7000 Sequence Detection System.

The PCR reaction cycle was (60° C. for 2 minutes)×1, then (95° C. for 10 minutes)×1, and then (95° C. for 15 seconds to 60° C. for 1 minute)×50. Table 2 shows primer sequences (forward: sequence number 1, and reverse: sequence number 2) used in the Determinate Quantity RT-PCR.

TABLE 2

| Gene | Gen bank Accession No. | | Primer Sequence |
|---|---|---|---|
| P450scc (Cyp11a) | AH002151 | Forward Reverse | GAGAAGCCTATCTTCTTCAACTTCA TGCAGCCTGCAATTCATACAGT |

In this method, GAPDH and eukaryotic initiation factors 1α1 (EF-1) were used as internal standard genes of gene expression. The expression of each gene was calculated by subject gene expression divided by internal standard gene expression and shown as relative values with a value of the control dietary group as 1.

IV P450scc Protein Level Measurement using Western Blot Method

Biological Tissue Samples and Antibodies

Testes of each of the above-described group that had been stored at −80° C. after dissection were used. Anti-P450scc antibodies were purchased from Chemicon International, Inc.

Tissue Homogenate Preparation

While being iced in 1 ml of 1× Phosphate buffered saline (PBS, including 10 µl of 100 mM phenyl methane sulfonyl fluoride [PMSF]), 0.2 g of testes were homogenized in the Polytron homogenizer (Biotron). Broken cells were removed by the testes being centrifuged at 3000 rpm for 5 minutes at 4° C. Supernate of the testes was collected to serve as the tissue homogenate. A portion of the tissue homogenate was used to determine the quantity of protein.

SDS-Processing of Samples

A hundred milliliters of 3×SDS buffer$^{(a)}$ was added to 200 µl of tissue homogenate, and the sample was left for 5 minutes in a boiling water bath. An SDS process was then performed.

SDS-PAGE

The sample to which the SDS process had been performed was diluted with 3×SDS buffer such that protein concentration was 1 µg/µl. Then, 15 µl of the sample was introduced to polyacrylamide gel$^{(b)}$ and electrophoresis$^{(c)}$ (100V for 90 minutes) was performed.

Transfer

After electrophoresis, three 3 MM papers (Whatman Plc) soaked in transfer buffer$^{(d)}$, gel, Immobilon™ (PVDF transfer membrane [Millipore Corporation] equalized in advance with methanol and transfer buffer), and three 3 MM papers were placed on a blotting pad from the anode side, and sandwiched between pads. The stack was then placed in a blotting bath (Bio-Rad Laboratories), and transfer was performed (250 mA for 180 minutes).

Blocking

After the transfer had been completed, the membrane was washed with TBS-T$^{(e)}$ and blocked for an hour in TBS-T (skim milk solution) including 5% skim milk.

Antibody Reaction

A primary antibody reaction was performed for an hour in a skim milk solution including the anti-P450scc antibodies (1/5000). A secondary antibody reaction was performed for an hour in a skim milk solution including anti-Rabbit IgG-HRP antibodies (1/5000). Anti-β-actin antibodies were used as control antibodies.

Detection and Analysis

One milliliter of ECL™ Western blotting detection reagent (Amersham Corp.) was poured over the entire membrane. The membrane was then reacted for five minutes in the dark. Luminescent signals were picked up by an Las-1000 Imaging System (Fujifilm Corp.) and quantity was determined using ImageGauge (trademark) image processing software.

(a) SDS Buffer 70 mM Tris-HCl (pH 6.8), 33 mM NaCl, 1 mM Na2EDTA, 2% SDS (w/v), 40 mM DTT, 0.01% bromophenol blue (w/v), and 10% glycerol (b) Polyacrylamide Gel Resolving gel: 12.5% acrylamide, 375 mM Tris-HCl (pH 8.8), 0.1% SDS, 0.05% TEMED, and 0.075% APS (w/v)

Concentrating gel: 3.8% acrylamide, 125 mM Tris-HCl (pH 6.8), 0.1% SDS, 0.05% TEMED, and 0.075% APS (w/v)

(c) Electrophoresis Buffer 25 mM Tris, 0.19M glycine, and 0.1% SDS (w/v)

(d) Transfer Buffer 48 mM Tris, 39 mM glycine, and 20% methanol (e) TBS-T Buffer 0.1M Tris-HCl (pH 7.5), 0.37M NaCl, and 0.5% Tween 20

Quantitative Analysis of Protein in Tissue Homogenates

Protein concentration in the tissue homogenates was measured by the Bradford method. Twenty microliters of suitably diluted sample solution was placed in an eppendorf tube. One milliliter of Bio-Rad protein assay diluted five times was added to the sample solution and mixed by the vortex. After the sample solution was left at room temperature for five minutes, absorbency at 595 nm was measured. A bovine serum albumin (BSA) was used as a standard curve.

V Testosterone Measurement

A following kit was used for the measurement.

Testosterone EIA Kit (Cayman Chemical Co.)

Preparation of Samples

Because materials inhibiting the assay may be included in the plasma and the testis homogenate, steroid hormones were extracted in advance using ether.

Extraction from Plasma

Zero-point-five milliliters of plasma was placed in a test tube. Two-point-five milliliters of diethyl ether was added to the test tube, and centrifugal separation was performed (3000 rpm at 4° C. for 5 minutes). After an ether layer (upper layer) formed by centrifugal separation had been collected, 2.5 ml of diethyl ether was again added to the plasma sample, and a similar process was performed.

The collected ether layer was dried under vacuum using a centrifugal vacuum concentrator (Taitec Corporation). The obtained concentrate was dissolved in 0.5 ml of EIA buffer included in the kit. The dissolved concentrate served as the plasma sample.

Extraction from Testis

A hundred milligrams of testis tissue was homogenized in the Polytron homogenizer while being iced in 5 ml of phosphate buffered saline. One milliliter of the homogenate was placed in a test tube. Five milliliters of diethyl ether was added to the test tube and mixed for approximately one minute by the vortex, thereby performing centrifugal separation (3000 rpm at 4° C. for 5 minutes).

After an ether layer (upper layer) formed by centrifugal separation had been collected, 5 ml of diethyl ether was again added to the testis homogenate. The collected ether layer was dried under vacuum using the centrifugal vacuum concentrator (Taitec Corporation). The obtained concentrate was dissolved in 1 ml of EIA buffer included in the kit. The dissolved concentrate served as the testis sample.

VI Statistical Analysis

After difference among groups in data had been checked by one-way layout analysis of variance, Scheffe's multiple comparison test was performed on the data.

FIG. 1 shows analysis results of the concentrations of vitamin K1 (right) and MK-4 (left) in the testes of rats that had been administered the low K diet (no vitamin K added), the control diet (vitamin K1 of 0.75 mg/kg added), and the MK-4 added diet (MK-4 of 75 mg/kg added) for 35 days. In all examples, the vitamin K in the testes was confirmed to have changed to MK-4 regardless of administration form. Although no significant differences were observed between the low K dietary group and the control dietary group, MK-4 concentration in the MK-4 added dietary group was significantly high.

Figure 2:
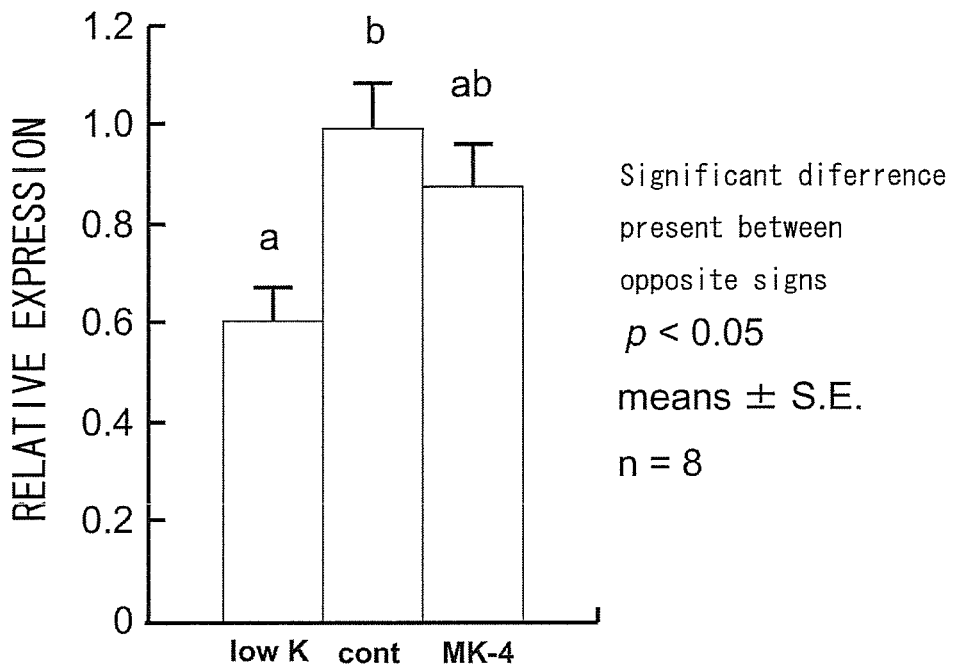
FIG. 2 is a diagram of a comparison of P450scc mRNA expression levels in the rats in FIG. 1.

FIG. 2 shows P450scc mRNA expression levels, the P450scc mRNA being steroid hormone synthetic pathway genes. Compared to the control dietary group and the MK-4 added dietary group, the expression level was slightly lower in the low K dietary group.

Figure 3:
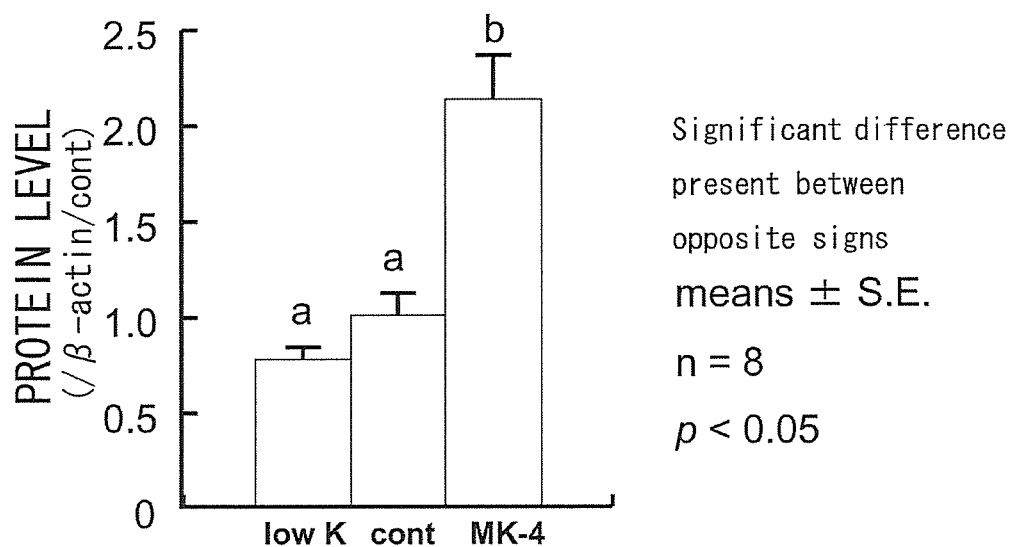
FIG. 3 is a diagram of a comparison of P450scc protein levels in the rats in FIG. 1.

FIG. 3 shows P450scc protein levels. Changes between the control dietary group and the low K dietary group were not observed. However, the protein level was significantly higher in the MK-4 added dietary group.

Figure 4:
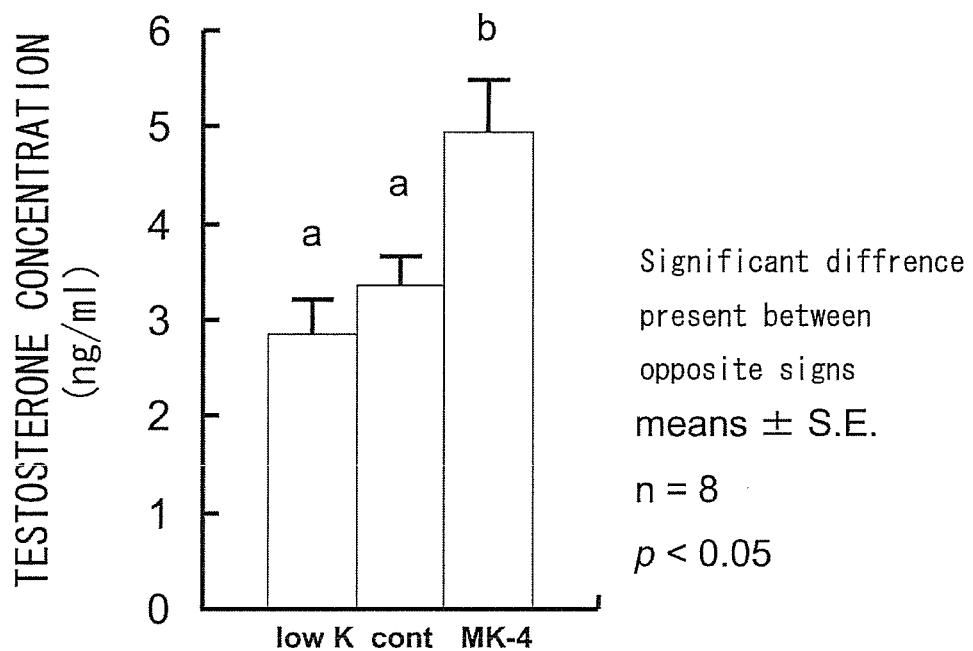
FIG. 4 is a diagram of a comparison of plasma testosterone concentrations in the rats in FIG. 1.

FIG. 4 shows plasma testosterone concentration. Compared to the control dietary group, the plasma testosterone concentration was significantly higher in the MK-4 dietary group.

From the above-described results, it is clear that blood testosterone levels increase by vitamin K being administered. The vitamin K concentration in the control diet is a required amount of vitamin K and is an amount that can be ingested by an ordinary diet. It is thought that decrease in testosterone levels due to insufficient vitamin K rarely occurs. On the other hand, as a result of vitamin K being actively ingested in adherence to the invention, the blood testosterone increased. Therefore, when the blood testosterone decreases for some reason, the blood testosterone can be increased by intake of vitamin K.

Example 2

Materials and Methods

As in Example 1, the experimental animals and breeding conditions were ordinary rats (Wistar/Std, eight-week-old males) bred in a breeding room set to a temperature of 23° C., humidity of 50±5%, and a 12-hour light/dark cycle in which lights were turned on at 8 AM and turned off at 8 PM.

As experimental dietary groups, the following three groups were provided.
(1) Control dietary group (vitamin K1 of 0.75 mg/kg was added)
(2) Vitamin K1 added dietary group (vitamin K1 of 75 mg/kg was added)
(3) MK-4 added dietary group (menaquinone-4 of 75 mg/kg was added)

Vitamin K1 was purchased from Wako Pure Chemical Industries, Ltd. Menaquinone-4 from Nisshin Pharma Inc. was used. Vitamin K1 or menaquinone-4 was added to each experimental diet to achieve the composition proportions shown in Table 1 and evenly mixed.

The breeding period was 35 days. Blood was drawn from tail veins every week at 18 o'clock. Measurements of weight, diet intake, testis vitamin K content, testis testosterone concentration, and plasma testosterone concentration were taken. The analysis method was similar to that in Example 1.

Statistical Analysis

Data on testis vitamin K concentration and testosterone concentration was analyzed using the Tukey method. Analysis of changes over time in the blood testosterone concentrations was performed by two-way layout analysis of variance (repeated). In all cases, significant differences was P<0.05.

Results

Figure 5:
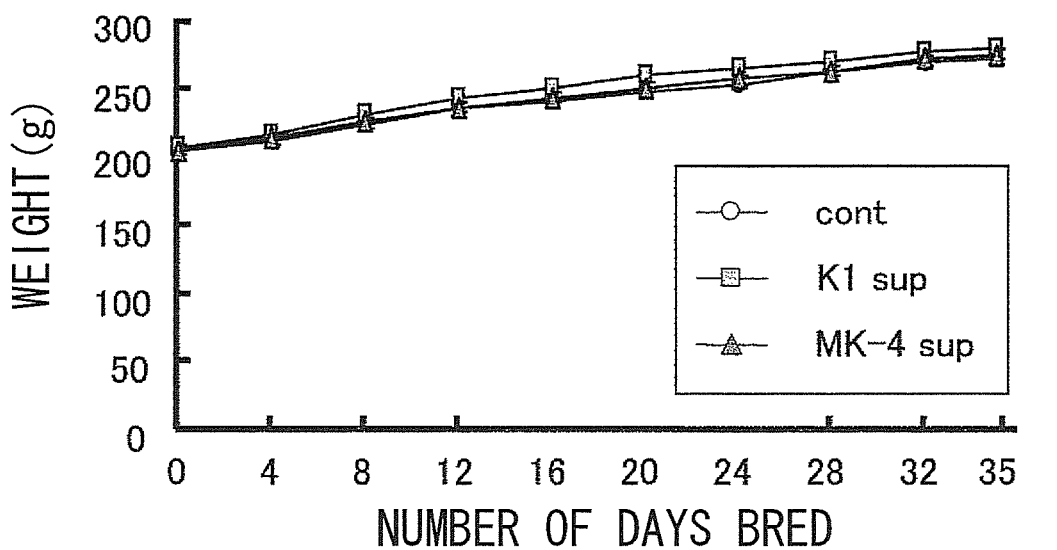
FIG. 5 is a diagram of daily variations in weight when rats are administered a vitamin K1-added dietary group in adherence to Example 2, and a control dietary group as comparison example.
Figure 6:
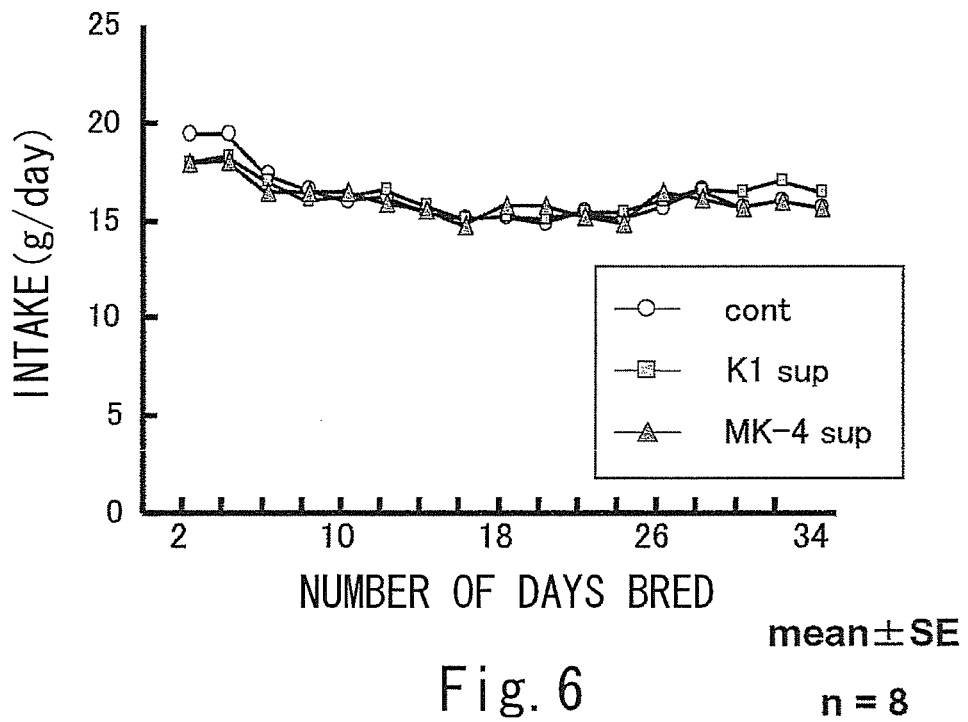
FIG. 6 is a diagram of daily variations in intake in the rats in FIG. 5.

Differences in weight and diet intake could not be observed between the control dietary group (vitamin K1 of 0.75 mg/kg added), the vitamin K1 added dietary group, and the MK-4 added dietary group (FIG. 5 and FIG. 6).

Figure 7:
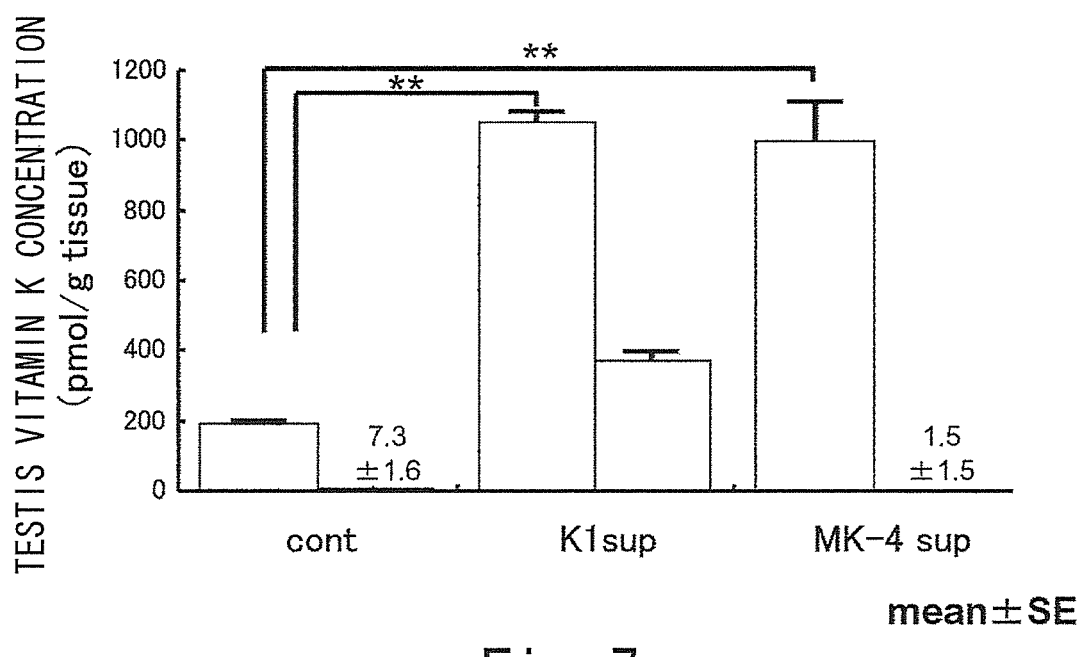
FIG. 7 is a diagram of a comparison of testis vitamin K concentrations in the rats in FIG. 5.

FIG. 7 shows the results of testis vitamin K concentration (right: vitamin K1, and left: MK-4). The testis MK-4 concentration significantly increased in the vitamin K1 added dietary group and the MK-4 added dietary group. It is thought that vitamin K1 was converted to MK-4 in the body.

Figure 8:
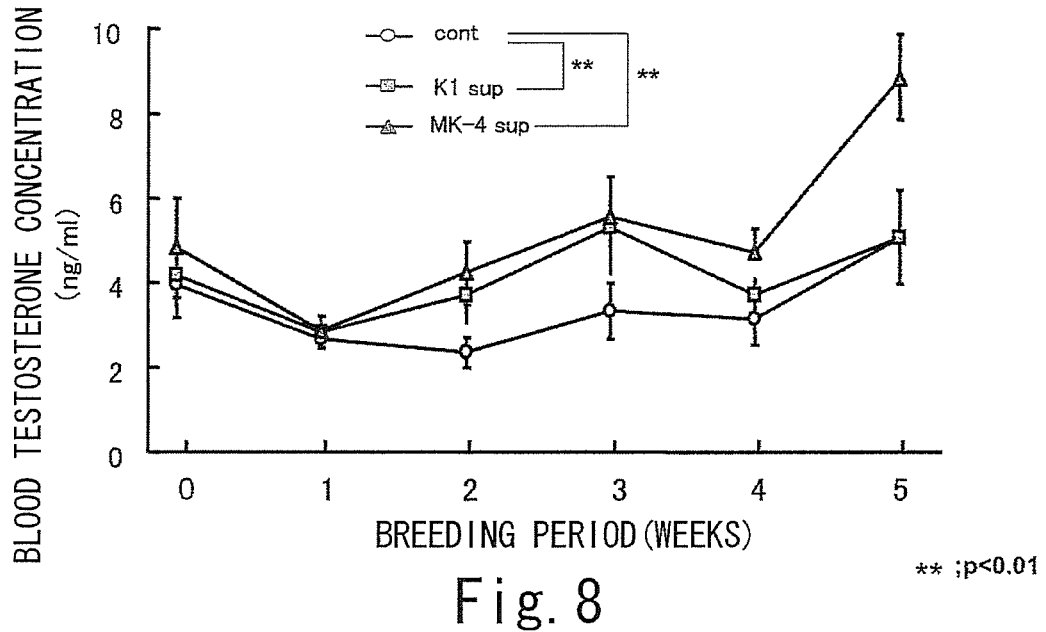
FIG. 8 is a diagram of changes in blood testosterone value in the rats in FIG. 5.

FIG. 8 shows changes in blood testosterone values. The blood testosterone values of the vitamin K1 added dietary group was not seen to differ from those of the control dietary group at four weeks and five weeks. At two weeks and three weeks, the blood testosterone values of the vitamin K1 added dietary group was higher than those of the control dietary group. When an overall two-way layout analysis of variance was performed, the significant difference was determined to be P<0.01.

Figure 9:
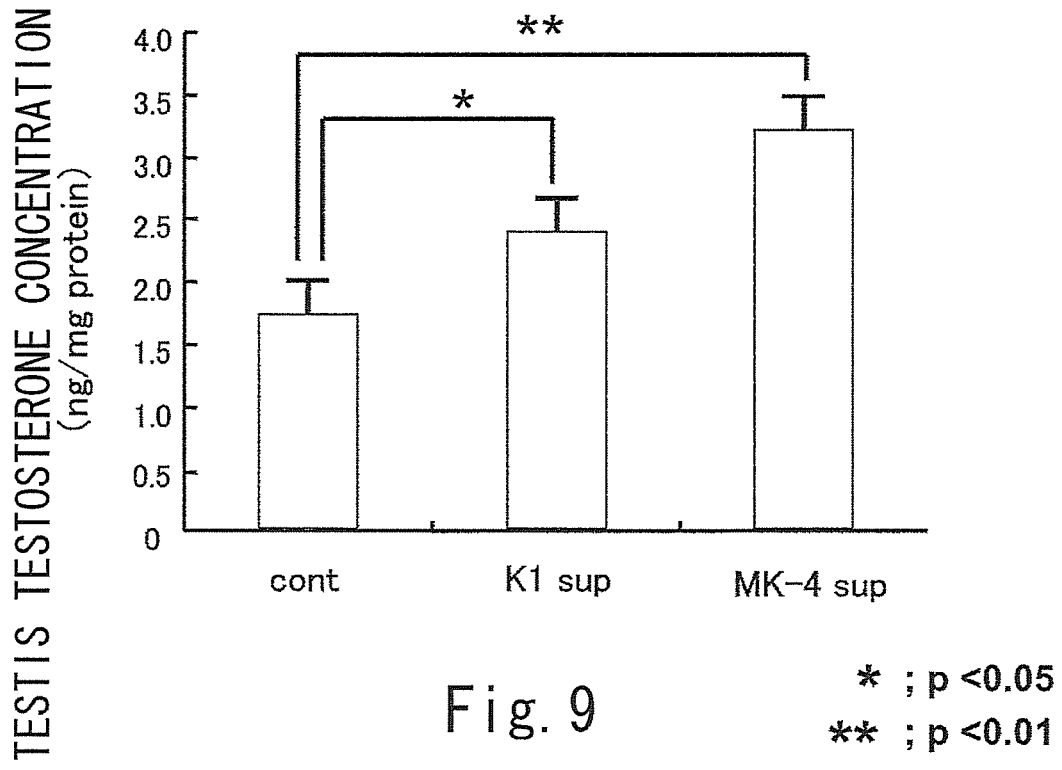
FIG. 9 is a diagram of a comparison of testis testosterone concentrations in the rats in FIG. 5.

FIG. 9 shows testis testosterone concentration results. The testosterone values were high in both the vitamin K1 added dietary group and the MK-4 added dietary group.

From the above-described results, it is clear that vitamin K1 and vitamin K2 (menaquinone-4) increase the blood testosterone level and the testis testosterone level. Administration of vitamin K2 is preferable. Because changes in weight and changes in diet intake are not seen, increase of testosterone using vitamin K can be said to be a highly safe method.

Preferred embodiments of the invention were described in detail above. However, it is understood that changes and modifications within the scope of the invention and the scope of the spirit of the invention can be made, by a person skilled in the art taking into consideration the disclosure in the application. The embodiments of the invention are as follows:

1. A testosterone enhancer including vitamin K as an active ingredient.
2. The testosterone enhancer according to the above-described item 1, in which the vitamin K content is 0.0001% by weight to 100% by weight.
3. The testosterone enhancer according to the above-described item 1, in which the above-described vitamin K is vitamin K2.
4. The testosterone enhancer according to the above-described item 1, in which the vitamin K is menaquinone-4 and/or menaquinone-7.
5. Medicines that prevent, improve, and/or treat symptoms or diseases caused by decreased testosterone, made from a testosterone enhancer including vitamin K as an active ingredient.
6. The medicines according to the above-described item 5, in which the symptoms and diseases are deterioration in muscles, cognitive functions, concentration, motivation, blood vessel flexibility, lipid metabolism, reproductive functions, male sexual functions, and micturition.
7. Supplements, health foods, and functional foods that include a testosterone enhancer including vitamin K as an active ingredient.

8. The supplements, health foods, and functional foods according to the above-described item 7, used to prevent, improve and/or treat deterioration in muscles, cognitive functions, concentration, motivation, blood vessel flexibility, lipid metabolism, reproductive functions, male sexual functions, and micturition.

9. A method of preventing, improving, and/or treating symptoms or diseases caused by decreased testosterone, involving administration of an effective dose of a testosterone enhancer including vitamin K as an active ingredient.

10. The method according to the above-described item 9, in which the vitamin K content is 0.0001% by weight to 100% by weight.

11. The method according to the above-described item 9, in which the vitamin K is vitamin K2.

12. The method according to the above-described item 9, in which the vitamin K is menaquinone-4 or menaquinone-7, or both.

13. The method according to the above-described item 9, in which the symptoms and diseases are deterioration in muscles, cognitive functions, concentration, motivation, blood vessel flexibility, lipid metabolism, reproductive functions, male sexual functions, and micturition.

14. A usage of vitamin K for manufacturing a testosterone enhancer that prevents, improves, and/or treats symptoms or diseases caused by decreased testosterone.

15. The usage according to the above-described item 14, in which the vitamin K content is 0.0001% by weight to 100% by weight.

16. The usage according to the above-described item 14, in which the vitamin K is vitamin K2.

17. The usage according to the above-described item 14, in which the vitamin K is menaquinone-4 and/or menaquinone-7.

18. The usage according to the above-described item 14, in which the symptoms and diseases are deterioration in muscles, cognitive functions, concentration, motivation, blood vessel flexibility, lipid metabolism, reproductive functions, male sexual functions, and micturition.

The invention claimed is:

1. A method of improving symptoms of, or treating male age-related hypogonadism, including a step of administering a composition comprising vitamin K chosen from the group consisting of vitamin K1 and vitamin K2 to a man who is suffering from male age-related hypogonadism to increase testosterone.

2. The method of claim 1, wherein vitamin K2 is chosen from the group consisting of menaquinone-4, menaquinone-7, and combinations thereof.

* * * * *

SEQUENCE LISTING

```
<160> NUMBER OF SEQ ID NOS: 2

<210> SEQ ID NO 1
<211> LENGTH: 26
<212> TYPE: DNA
<213> ORGANISM: Artificial sequence
<220> FEATURE:
<223> OTHER INFORMATION: Forward primer typical of mould

<400> SEQUENCE: 1
gagaagccta tcttcttcaa cttcca                                            26

<210> SEQ ID NO 2
<211> LENGTH: 22
<212> TYPE: DNA
<213> ORGANISM: Artificial sequence
<220> FEATURE:
<223> OTHER INFORMATION: Reversal primer typical of mould

<400> SEQUENCE: 2
tgcagcctgc aattcataca gt                                                22
```